United States Patent [19]

Fullington et al.

[11] Patent Number: 5,142,070
[45] Date of Patent: Aug. 25, 1992

[54] PROCESS FOR THE DIRECT OXIDATION OF PROPYLENE TO PROPYLENE OXIDE

[75] Inventors: Michael C. Fullington, Lake Charles; Buford T. Pennington, Sulphur, both of La.

[73] Assignee: Olin Corporation, Cheshire, Conn.

[21] Appl. No.: 620,675

[22] Filed: Dec. 3, 1990

[51] Int. Cl.$^5$ ............................................. C07D 301/06
[52] U.S. Cl. ..................................... 549/532; 549/523
[58] Field of Search ................................ 549/532, 523

[56] References Cited

U.S. PATENT DOCUMENTS

| | | | |
|---|---|---|---|
| 1,995,991 | 3/1935 | Lenher | 549/523 |
| 2,392,316 | 1/1946 | Dreyfus | 549/523 |
| 2,530,509 | 11/1950 | Cook | 549/523 |
| 2,689,253 | 9/1954 | Robertson et al. | 549/523 |
| 3,132,156 | 5/1964 | Lemon et al. | 549/523 |
| 3,483,229 | 12/1969 | Bernard | 549/523 |
| 3,625,847 | 12/1971 | Weisbeck | 204/169 |
| 4,785,123 | 11/1988 | Pennington | 549/523 |
| 4,882,443 | 11/1989 | Pennington | 549/532 |
| 4,883,889 | 11/1989 | Pennington | 549/532 |
| 4,885,374 | 12/1989 | Pennington | 549/532 |
| 4,943,643 | 7/1990 | Pennington et al. | 549/532 |
| 4,959,486 | 9/1990 | Pennington | 549/532 |

Primary Examiner—C. Warren Ivy
Assistant Examiner—A. Owens
Attorney, Agent, or Firm—Dale Lynn Carlson

[57] ABSTRACT

Described herein is a process for the direct oxidation of propylene to propylene oxide in conditions such that propylene is above its critical temperature and pressure.

8 Claims, No Drawings

PROCESS FOR THE DIRECT OXIDATION OF PROPYLENE TO PROPYLENE OXIDE

BACKGROUND OF THE INVENTION

1. Field of the Invention

This invention relates to a process for the direct oxidation of propylene to propylene oxide under conditions such that propylene is above its critical temperature and pressure. Under such conditions the selectivity of propylene to propylene oxide is enhanced. The instant process does not require the use of a solvent or catalyst.

2. Brief Description of Prior Art

Propylene has been directly oxidized to propylene oxide under a variety of different conditions. This is illustrated by the following patents:

U.S. Pat. No. 1,995,991 describes the direct oxidation of olefin hydrocarbons. In Example III of the patent, propylene oxide is prepared by the reaction of propylene and oxygen at a temperature of from 270°-360° C. for a reaction time of 28 seconds. The patent states that the size and shape of the reaction vessel is important and that yield of product is increased by increasing the ratio of free space to surface. On page 4, lines 9 to 15 it is stated that it is preferred to operate at atmospheric pressure although pressures greater than one atmosphere can be used and 250° C.

U.S. Pat. No. 2,392,316 generally describes the oxidation of hydrocarbons. The patent states that one volume of a gaseous unsaturated hydrocarbon is mixed with about 7 volumes of air and heated to a temperature of 400° to 800° F. while under a super-atmospheric pressure of nor more than 500 pounds per square inch.

U.S. Pat. No. 2,530,509 describes the production of propylene oxide by direct oxidation which comprises reacting at a temperature of about 275° C. to about 700° C. a hydrocarbon gas selected from propane and propylene with a gas containing molecular oxygen in an amount to give in the total gas mixture a molar ratio of hydrocarbon to oxygen of at least 2 and not more than 20. The gasses are stated to be confined in a reaction zone having a ratio of area of gas contacting surface to volume of free space of at least 5 square centimeters per cubic centimeter. The patent states in column 6, lines 39-43 that the reaction itself takes place in a relatively short time and space and that it is difficult if not impossible to lengthen the reaction time.

Further, it is stated in column 5, lines 48-53 that operating pressures below 200 pounds per square inch absolute obtain the maximum efficiencies and yields.

U.S. Pat. No. 2,689,253 is directed to the oxidation of hydrocarbons. Examples IV-VI describe the oxidation of propylene and propane. These examples describe the reaction of propylene or a mixture of propane and propylene with oxygen to give a vapor phase partial oxidation. The reactions are carried out at temperatures of 650° F. under a pressure of about 100 pounds per square inch gauge to initiate reaction. After initiation, it is stated that the temperature rises to about 850°-900° F. and further reaction is halted within about 0.5 seconds by passing the reaction mixture into a cascading stream of water.

U.S. Pat. No. 3,132,156 is directed to the selective non-catalytic vapor phase oxidation of saturated aliphatic hydrocarbons to olefin oxides. This patent describes the preparation of propylene oxide. It is stated in the patent that the reaction is conducted in such a manner that a critical balance is maintained between temperature, pressure, oxygen, and contact time in a critical environment of reactants, products and temperature gradients in the reaction zone (Column 2, line 68 through line 2 of column 3). Further, the following is stated in column 8, line 73 through line 2 of column 9:

'However, it has been discovered that all the relationships previously set forth are to no avail unless the oxidation takes place at pressures about 20 to 150 p.s.i.g.'

U.S. Pat. No. 3,483,229 relates to the non-catalytic vapor phase oxidation of hydrocarbons in a dilution reactor. The examples of this patent describe the reaction of a mixture of propane and propylene with oxygen in a dilution reactor. The reaction is carried out at a temperature ranging from about 425° C. to about 575° C. and a pressure of from about 20 p.s.i.g. to about 150 p.s.i.g.

U.S. Pat. No. 3,625,847 is directed to the direct oxidation of propylene to propylene oxide. The patent states that a gaseous mixture of propylene together with a gas selected from air, oxygen, nitrous oxide and mixtures thereof is fed to an electrical alternating current gas discharge which is stated to be of such nature that the electrical alternating field is applied perpendicularly to the direction of flow of the gas mixture. The gas discharge is electrically in series with a dielectric of high dielectric constant and comes into contact with the gas discharge plasma of the dielectric and in which the gas mixture containing propylene-1,2-oxide continuously leaves the discharge chamber.

SUMMARY OF THE INVENTION

The present invention is directed to an improved process for the direct oxidation of propylene to propylene oxide under conditions such that propylene is above its critical temperature and pressure. Under these conditions the selectivity to propylene oxide is increased.

In the instant invention, propylene is reacted with oxygen or an oxygen containing gas at a temperature of about 100°-300° C., preferably from about 150°-275° C., and most preferably from 170°-260° C. The pressure the reaction is carried out is above 300 p.s.i.a., preferably from 650-3,000 p.s.i.a. The reaction is generally carried out in any reactor capable of carrying out the reaction under the stated reaction conditions. The reactor may be immersed in a molten salt bath to control the temperature of the reactor. These molten salts include one or more molten nitrate salts such as sodium nitrate, potassium nitrate, calcium nitrates, sodium nitrite, potassium nitrate, and the like.

Reactor residence time is generally from about 0.1 to 10,000 seconds, preferably from about 5 to 5,000 seconds, and most preferably from about 10 to 3,000 seconds. The composition of the gas fed to the reactor generally contains from about 40 to 95 volume percent propylene. The oxygen or oxygen containing portion of the gas content is from about 2 to 15, preferably from about 3 to 10 volume percent.

In one embodiment of this invention a coproduct produced by the oxidation reaction, i.e., acetaldehyde may be recycled to the oxidation reaction.

EXAMPLES

The following examples serve to give specific illustrations of the practice of this invention, but they are not intended in any way to limit the scope of this invention.

EXAMPLE I

A feed gas stream consisting of 30 volume percent propylene, 5 volume percent oxygen, and 45 volume percent nitrogen is fed to a ¼ inch diameter stainless steel coil reactor 12 feet long at the rate of 4,000 cubic centimeters per minute. The coil reactor is submerged in a molten nitrate salt bath at 200° C. The coil is setup as a continuous flow through reactor, which under the conditions described has a residence time of about 210 seconds. The reaction pressure is maintained at 1500 p.s.i.g. by a backpressure regulator. Reaction off gas is sampled via a syringe through a heat traced double valving system equipped with a septum. Gas chromatographic analysis of the off gas shows that 60.8 moles of propylene oxide are formed for every 100 moles of propylene reacted. The per pass oxygen conversion is 97.5% and the per pass propylene conversion is 8.3%.

EXAMPLE II

A feed stream similar to that used in Example I is fed into a two liter autoclave reactor equipped with a double fan blade stirrer. The stirrer is set at 1000 RPM to maintain a well mixed condition inside the reactor. The reactor is operated as a continuous stirred tank reactor at 1500 p.s.i.g. and a gas temperature of 190° C. Heating is provided by external electrical heating coils. The reactor residence time is about 1700 seconds at the feed gas flowrate of 4000 cubic centimeters STP. The reactor contents are sampled via syringe and analyzed by GC methods. The analysis shows that 67.1 moles of propylene oxide is produced for every 100 moles of propylene consumed. The oxygen conversion is 80 percent and the propylene conversion is 6.5 percent.

EXAMPLE III

This example demonstrates the benefit of recycling the acetaldehyde coproduct to the reactor. A coil reactor is assembled as in Example I, and is operated as a continuous flow through reactor. The feed gas consists of 50 volume percent propylene, 5 volume percent oxygen, 44.5 volume percent nitrogen, and 0.5 volume percent acetaldehyde at a flow rate of 4000 cubic centimeters per minute. The coil is maintained at 220° C. using an external molten nitrate salt bath. The reaction pressure is maintained at 1500 p.s.i.g. by a backpressure regulator. Gas chromatographic analysis of the reaction off gas shows that 65.0 moles of propylene oxide are formed for every 100 moles of propylene that reacted. The per pass oxygen conversion is 98 percent and the per pass propylene conversion is 6.7 percent.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process for preparing propylene oxide by reacting propylene with oxygen and/or an oxygen containing gas in a reactor at a temperature of from about 100° to about 300° C. provided by an external heating source which is external to said reactor and at a pressure of 650 to 3,000 p.s.i.a.

2. A process as defined in claim 1, wherein the temperature is from about 150° to about 275° C.

3. A process as defined in claim 1, wherein the reaction is carried out for about 0.1 to about 10,000 seconds.

4. A process as defined in claim 3, wherein the reaction is carried out for about 5 to 5,000 seconds.

5. A process as defined in claim 1, wherein the reaction is carried out in a reactor immersed in a molten salt.

6. A process as defined in claim 5, wherein the molten salt is selected from one or more of sodium nitrate, potassium nitrate, calcium nitrate, sodium nitrite and potassium nitrite.

7. A process as defined in claim 1, wherein the gas contains from about 40 to 95 volume propylene.

8. A process as defined in claim 1, wherein acetaldehyde is recycled to the oxidation reaction.

* * * * *